(12) United States Patent
Symes et al.

(10) Patent No.: US 7,901,915 B2
(45) Date of Patent: Mar. 8, 2011

(54) BIOCATALYTIC MANUFACTURING OF (METH) ACRYLIC ESTERS

(75) Inventors: Kenneth Charles Symes, Keighley (GB); Simon Andrew Collier, Halifax (GB); Yvonne Christine Armitage, Huddersfield (GB); Rajesh Mistry, Bradford (GB); Robert Baranyai, Brighouse (GB)

(73) Assignee: BASF SE, Ludwigshafen (DE)

( * ) Notice: Subject to any disclaimer, the term of this patent is extended or adjusted under 35 U.S.C. 154(b) by 434 days.

(21) Appl. No.: 11/991,446

(22) PCT Filed: Sep. 12, 2006

(86) PCT No.: PCT/EP2006/066260
§ 371 (c)(1),
(2), (4) Date: Mar. 4, 2008

(87) PCT Pub. No.: WO2007/039415
PCT Pub. Date: Apr. 12, 2007

(65) Prior Publication Data
US 2009/0130729 A1    May 21, 2009

(30) Foreign Application Priority Data
Sep. 19, 2005  (EP) .................................. 05108603

(51) Int. Cl.
*C12P 7/62* (2006.01)
*C12P 7/40* (2006.01)

(52) U.S. Cl. ........................................ 435/135; 435/136

(58) Field of Classification Search ........................ None
See application file for complete search history.

(56) References Cited

U.S. PATENT DOCUMENTS

| 5,541,093 | A | 7/1996 | Hwang | 435/135 |
| 5,973,203 | A | 10/1999 | Egraz et al. | 564/135 |
| 6,485,947 | B1 | 11/2002 | Rajgarhia et al. | 435/139 |
| 7,186,541 | B2 | 3/2007 | Gokarn et al. | 435/232 |

FOREIGN PATENT DOCUMENTS

| WO | 00/71738 | 11/2000 |
| WO | 02/42418 | 5/2002 |
| WO | 02/42471 | 5/2002 |

OTHER PUBLICATIONS

Zhang et al.; Protein Engineering; vol. 16, No. 8 (Aug. 2003) pp. 599-605.
Rotticci-Mulder et al.; Protein Expressions and Purification, vol. 21, No. 3 (Apr. 2001) pp. 386-392.
Athawale et al., Journal of Molecular Catalysis B Enzymatic, vol. 10, No. 6 (Nov. 2000) pp. 551-554.
Patel et al., Analytical Biochemistry, Academic Press, vol. 170, No. 2 (1988) pp. 355-360.
O'Sullivan et al., Biochimica et Biophysica Acta, vol. 450, No. 3 (1976) pp. 410-417.
Th.Willke and K.-D. Vorlop, Appl. Microbiol. Biotechnol. (2004) 66:131-142).
Dalal et al.; Biosources Digest vo. 2 p. 89 to 97 (1980).
Lehninger, A.L., Biochemistry, $2^{nd}$ Edition, 1975, Worthe Publishers Inc. NY, p. 343.

Primary Examiner — Herbert J. Lilling
(74) *Attorney, Agent, or Firm* — Shiela A. Loggins

(57) ABSTRACT

The invention relates to a biocatalytic method or process for the synthesis of esters of acrylic acid and/or methacrylic acid free of positively chargeable/charged groups, comprising reacting one or more alcohols (alcohol starting materials) which are free of positively chargeable or charged groups with (meth)acrylyl-CoA, preferably in the presence of a catalyst (inorganic, organic or organometallic, or preferably a biocatalyst) capable of effecting the transfer of an alcohol radical from an alcohol starting material as defined above or below to (meth)acrylyl CoA under removal of the CoA moiety transferase activity, such as an enzyme of the transferase or hydrolase class of enzymes. The (meth)acrylyl-CoA is preferably formed by reaction of (meth)acrylic acid or its salts with coenzyme A in the presence of an energy providing substance and a biocatalyst e.g. with S-acetyl coenzyme A synthetase activity or by reaction of acrylate or methacrylate produced metabolically in the presence of a biocatalyst or metabolically.

15 Claims, No Drawings

BIOCATALYTIC MANUFACTURING OF (METH) ACRYLIC ESTERS

The invention relates to a biocatalytic method or process for the synthesis of (one or more) esters of acrylic acid and/or methacrylic acid which are free of positively chargeable or charged groups, said method or process comprising reacting one or more alcohols (alcohol starting materials) which are free of positively charged groups with acrylyl-CoA and/or methacrylyl-CoA, preferably in the presence of a catalyst, which can be an inorganic, organic or organometallic catalyst, or preferably a biocatalyst, especially a biocatalyst capable of effecting the transfer of an alcohol radical from an alcohol starting material as defined above or below to (meth) acrylyl CoA under removal of the CoA moiety (e.g. using transferase activity), such as an enzyme of the transferase or hydrolase class of enzymes. The (meth)acrylyl-CoA is preferably formed by reaction of (meth)acrylic acid or its salts such as sodium acrylate with coenzyme A in the presence of an energy providing substance and a biocatalyst with synthetase (in particular CoenzymeA synthetase, especially S-acetyl Coenzyme A synthetase) activity) or by reaction of acrylate or methacrylate that has been produced metabolically, for example from sugars e.g. via lactate by a microorganism; to (especially transformed, that is genetically modified) organisms capable of effecting the transfer of an alcohol radical from an alcohol starting material as defined above or below to (meth)acrylyl CoA under removal of the CoA moiety and preferably in addition having synthetase (in particular CoenzymeA synthetase, especially S-acetyl Coenzyme A synthetase) activity, and their use in said process or method; the use of a biocatalyst capable of effecting the transfer of an alcohol radical from an alcohol starting material as defined above or below to (meth)acrylyl CoA under removal of the CoA moiety to carry out said transfer, in order to manufacture one or more of the esters mentioned above; and to further uses, organisms, processes and methods as described below.

The microbially or biocatalytically mediated conversion of biomass, e.g. cellulose or starch, to provide chemical raw materials, also in industrially useful quantities, represents an important alternative to fossil fuels and the production of fuels and other bulk chemical products in biorefineries is becoming of increasing importance in view of the future exhaustion of fossil fuels and the societal and political pressures to reduce carbon emissions due to the linked global climate changes taking place. Therefore it is important to have to hand as many biologically catalysed reactions as possible to allow for the use of biological or biocatalytic processes for their production, especially from replenishable, carbon neutral substrates such as crop derived carbohydrates.

For example, the lower (e.g. $C_1$-$C_7$) alkyl esters of acrylic acid and in particular methyl, ethyl and n-butyl acrylate are known as industrially useful esters. Acrylic esters are at present manufactured by the esterification of acrylic acid. Acrylic acid is made from the petrochemical propylene via an energy intensive 2-step oxidation process on a very large scale (>2 mio tonnes per annum worldwide). More than half of this production is converted to the mentioned or other esters, with the majority of this being the n-butyl ester. These monomers are used in the manufacture of polymers for a very wide range of applications including paints, lacquers, inks, adhesives, thickeners to name but a few. The manufacture of the acrylate esters requires considerable investment in plant and is an energy intensive process.

Instead of such what are basically chemical reactions, a biocatalytic reaction would be highly desirable in order to provide an integrated biosynthetic approach that may also make use of renewable or waste biomass.

U.S. Pat. No. 5,541,093 described the preparation of such an ester from the reaction of alcohol with organic acid in the vapour state at a temperature of from 25 to 55° C. in the presence of lipase. These esters include ethyl acetate and ethyl propionate. U.S. Pat. No. 5,973,203 describes a process for preparing (meth)acrylic acid amides by aminolysis of (meth)acrylic acid esters using lipase.

Additionally, the bio-production of ethanol for fuel has increased dramatically and in 2001 it was reported to stand at 30 billion litres (Th. Willke and K.-D. Vorlop, Appl. Microbiol. Biotechnol. (2004) 66:131-142). According to these authors, n-butanol was produced up until the era of cheap oil (1930) by fermentation from biomass and currently could again be produced biotechnologically as a fuel additive at competitive costs.

Therefore there is a clear need and an opportunity to produce acrylic (and methacrylic) esters on a significantly large scale in for example a biorefinery operation where the production of the alcohol is followed by coupling to acrylic acid via acrylyl CoA produced metabolically to yield the esters in a wholly green and sustainable way.

The metabolic synthesis of acrylic acid was described by Dalal et al (Biosources Digest vo. 2 p 89 to 97) in 1980. The authors reported that acrylyl CoA is hypothesised to be an intermediate in the anaerobic dehydration of lactate in *Megasphera elsdenii* and *Clostridium propionicum* and that it also occurs following β-hydroxypropionyl CoA dehydration in *Clostridium propionicum*. They also suggested that in a reaction using resting cells of *C. propionicum* acrylate accumulation was observed with propionate as the substrate. A metabolic scheme for the synthesis of acrylyl CoA is given in Scheme 1.

Scheme I: Metabolic pathways involving Acrylyl-CoA in Clostridium propionicum (see also Dalal et al., loc. cit.).

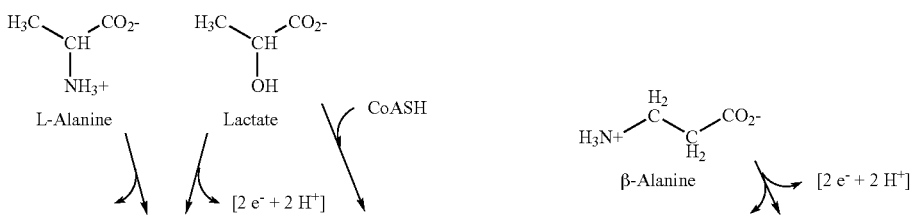

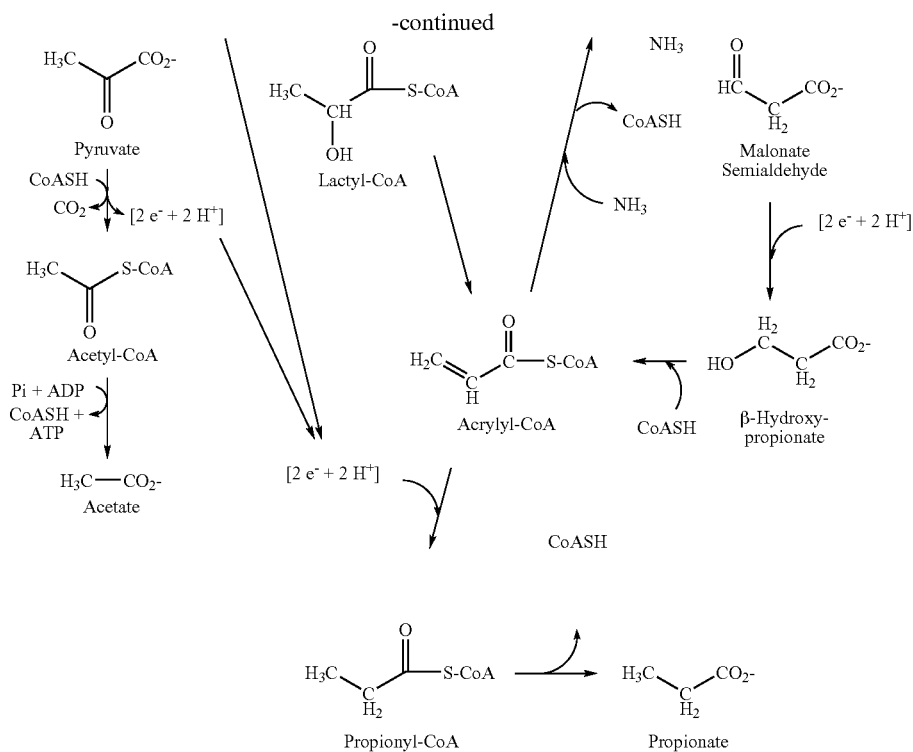

More recently, a few ways for the biosynthetic preparation of acrylate and acrylic esters have been described, e.g. in WO 02/042418 A2 or WO 02/42471 A2, see also WO 00/71738 for the synthesis of acrylic acid.

None of these documents describes the possibility of manufacturing acrylic esters directly.

Acrylic and methacrylic acid are known substrates of the enzyme S-acetyl CoA synthetase (S-acetyl coenzyme A synthetase, acetate thiokinase or acetate:CoA ligase) (EC 6.2.1.1), however, previously the products found did not in the main appear to correspond to the acyl CoA thioesters—instead binding of two equivalents of CoA took place via both Michael addition to the double bond and thioester formation via the carbonyl of the acid, and thus a bis-adduct was found to be formed (see e.g. Patel and Walt, Anal. Biochem. 170, 355-60 (1988)). The bis-adduct has the following formula:

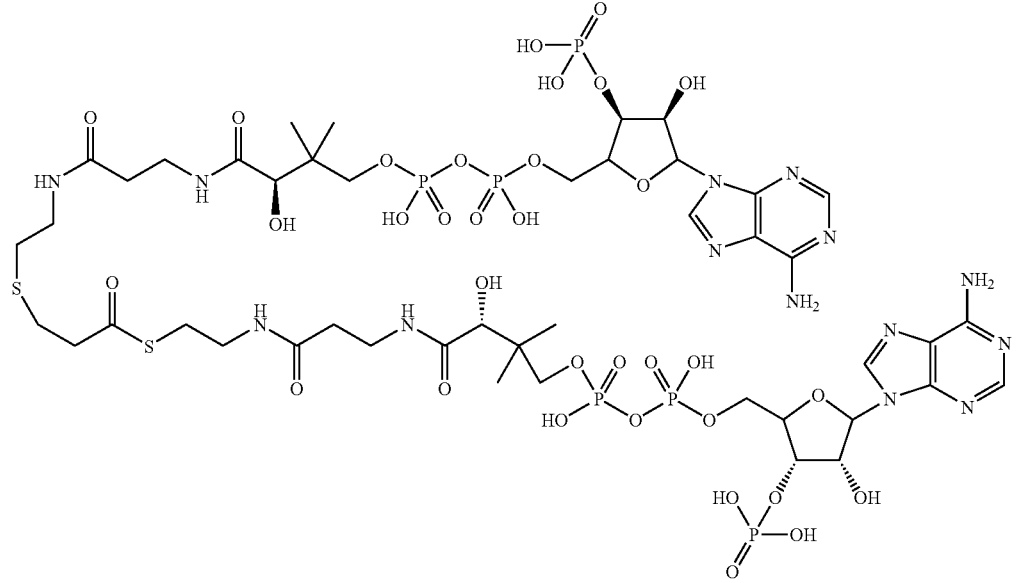

Against this background, it would be highly desirable to provide a biological process for the synthesis of (meth)acrylic esters that is simple and/or a real alternative to the present chemical methods and forms a basis also for the integration into a more general biotechnological process, e.g. finally making use of renewable resources.

Surprisingly it has now been found that it is possible to obtain (meth)acrylic esters which are free of positively charged groups, especially (meth)acrylic esters of lower alcohols, directly from S-(meth)acrylyl-Coenzyme A ((meth) acrylyl CoA) by reacting one or more alcohols which are free of positively charged groups with (meth)acrylyl-CoA, optionally or preferably in the presence of a catalyst, which can be an inorganic, organic or organometallic catalyst; or more preferably a biocatalyst capable of effecting the transfer of an alcohol radical from an alcohol starting material as defined above or below to (meth)acrylyl CoA under removal of the CoA moiety.

Even the synthesis of the precursor (meth)acrylyl CoA using (meth)acrylic acid or its salts, such as sodium acrylate, potassium acrylate, ammonium acrylate etc and Coenzyme A with the help of a biocatalyst having synthetase activity is possible because it can be shown that conditions are available where reaction of the carboxyl group of the (meth)acrylic acid or (meth)acrylic acid salt with the thiol group of Coenzyme A is favoured over addition to the double bond so that relatively more of the thioester than of the double bond adduct or bis-adduct can be formed, already in vitro using a biocatalyst that has synthetase activity e.g. by optimising the concentration of reactants, especially relatively to each other. Especially preferred in this regard is a fed-batch process described in more detail below.

The surprising new insight that in vitro conditions allow for the synthesis of (meth)acrylyl Coenzyme A forms the basis of (meth)acrylic ester synthesis also in vivo or by a combination of in vitro an in vivo steps.

This forms the basis of biosynthetic routes for the synthesis of acrylic esters that largely removes the dependency on petrochemical feedstocks, for example also by a combination of (meth)acrylyl-CoA synthesis in vivo or in vitro and ester synthesis in vitro or synthesis of ester with both steps in vivo.

The invention, in a first aspect, relates to a process or method for the manufacture of an ester or esters of acrylic acid and/or methacrylic acid which are free of positively chargeable or charged groups, especially of n-butyl(meth) acrylate (very preferred), ethyl(meth)acrylate (preferred), methyl(meth)acrylate (preferred), or further n-propyl, isopropyl, isobutyl, sec-butyl, tert-butyl, 2-ethylbutyl, n-pentyl, isopentyl, 1-methylpentyl, 1,3-dimethylbutyl, n-hexyl, isoheptyl, 1-methylhexyl, 2-ethylhexyl, stearyl or 2-hydroxy ethyl (meth)acrylate, or mixtures of two or more of these, said process comprising reacting one or (less preferably) more alcohols which are free of positively chargeable or charged groups, especially n-butanol (very preferred) or ethanol (preferred), or methanol (preferred), or further n-propanol, isopropanol, isobutanol, sec-butanol, tert-butanol, 2-ethylbutanol, n-pentanol, isopentanol, 1-methylpentanol, 1,3-dimethylbutanol, n-hexanol, isoheptanol, 1-methylhexanol, 2-ethylhexanol, stearyl alcohol or 2-hydroxyethanol with (meth)acrylyl-CoA optionally or preferably in the presence of a catalyst, which can be an inorganic, organic or organometallic catalyst; or preferably a biocatalyst capable of effecting the transfer of an alcohol radical from an alcohol starting material as defined above or below to (meth)acrylyl CoA under removal of the CoA moiety. Depending on the starting materials, the corresponding products or product mixtures are obtainable.

In addition, amides may also be manufactured by the reaction of (meth)acrylyl CoA with an amine to give the corresponding amide. Amides can include but are not limited to dimethylacrylamide, isopropylacrylamide, n-butylacrylamide, amylacrylamide, dimethylaminopropyl(meth)acrylamide.

In a further aspect, the invention relates to a genetically modified organism (GMO) transformed with one or more (preferably recombinant) nucleic acids comprising one or more sections coding for and allowing the expression of a biocatalyst capable of effecting the transfer of an alcohol radical from an alcohol starting material as defined above or below to (meth)acrylyl CoA under removal of the CoA moiety.

In another aspect, the invention relates to the use of a GMO as mentioned in the last paragraph for the manufacture of one or more esters of acrylic acid and/or methacrylic acid which are free of positively chargeable or charged groups, especially those defined above or below, comprising administering one or more appropriate starting materials derived from biomass and preferably also the corresponding alcohol(s) which is or are free of positively chargeable or charged groups, especially those defined above or below, to a culture of said microorganism and isolating the resulting (meth)acrylic ester(s).

The invention also relates to the (in vitro and/or in vivo) use of a biocatalyst capable of effecting the transfer of an alcohol moiety from an alcohol starting material as defined above or below to (meth)acrylyl CoA under removal of the CoA moiety to carry out the transfer of the (meth)acrylyl moiety from (meth)acrylyl CoA to n-butanol to manufacture n-butyl acrylate (very preferred) or ethanol to manufacture ethyl acrylate (preferred), or methanol to manufacture methyl acrylate (preferred) or 2-hydroxyethanol to manufacture 2-hydroxyethylmethacrylate or similar reaction of other alcohol to manufacture other ester(s). Also mixtures of alcohols can be used to obtain mixtures of esters.

The method or process according to the invention, in one embodiment, includes the use of a biocatalyst with synthetase activity for the manufacture of (meth) acrylyl CoA (especially with the corresponding reaction step taking place in vitro with a low level of bis-adduct formation. The synthetase can be any synthetase enzyme capable of effecting the formation of (meth)acrylyl CoA. It can, for instance, be a coenzyme synthetase, especially a coenzyme A synthetase. The term synthetase includes, but is not limited to an acyl synthetase, butyryl synthetase, propionyl synthetase or preferably acetyl S-Coenzyme A synthetase. Alternatively any synthetase capable of carrying out the reaction between acrylic acid or methacrylic acid or (meth)acrylic acid salts with CoA can be used.

The reaction forming the basis of the present invention can be represented by the following reaction scheme:

SCHEME II:

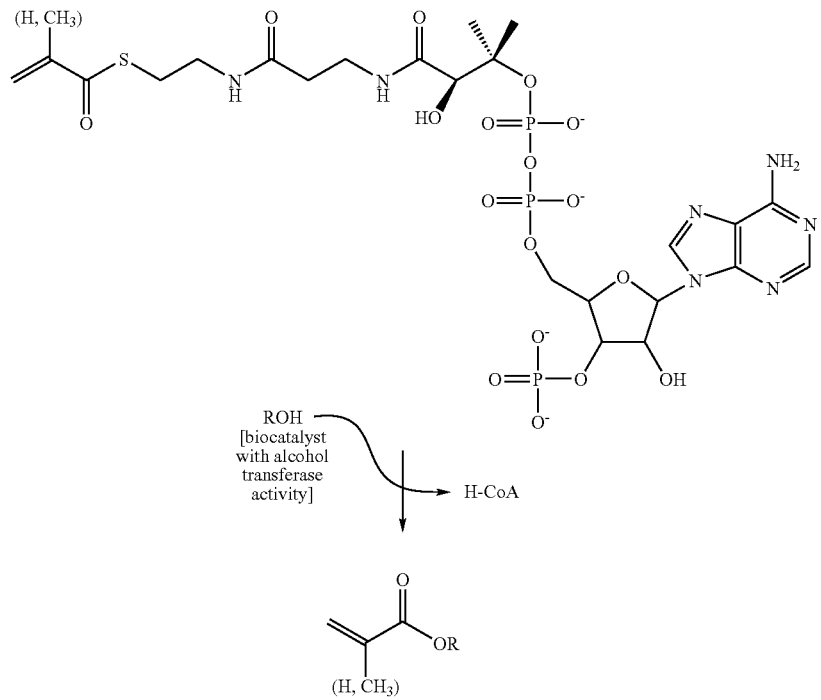

In Scheme II, the group R is the residue of an alcohol (without the H on the OH) of an alcohol free of positively chargeable or charged groups, especially as defined above or below.

Preferably, (meth)acrylyl-CoA is synthesized in vitro or in vivo from acrylic acid or methacrylic acid and/or salts. E.g. alkali metal salts thereof, such as the sodium salt thereof, commonly referred to as (meth)acrylate hereinafter, by means of a biocatalyst having synthetase activity, such as S-acetyl CoA synthetase activity (which is one preferred synthetase useful according to the invention) according to the following Scheme III:

SCHEME III:

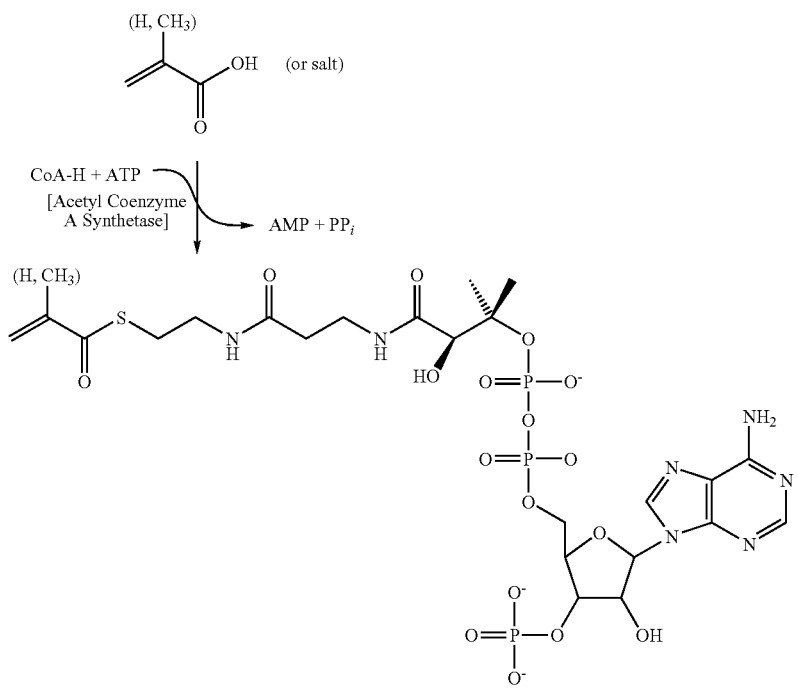

In contrast to the literature mentioned above, very surprisingly substantial amounts of (meth)acrylyl CoA can be obtained instead of the bis-adduct if the (in vitro) reaction conditions are modified appropriately, thus providing a contribution so that the method or process of the invention can result in good yields of the esters.

Thus it has turned out that the reaction can result in more of the desired (meth)acrylyl CoA if the molar ratios of (meth)acrylate and CoA are such that the (meth)acrylate is used in a molar excess, e.g. a more than 2-fold molar excess, more preferably in a more than 4-fold molar excess, still more preferably in a more than 10-fold, e.g. an approximately 15-fold molar excess of (meth)acrylate over the CoA; for example, the concentration of (meth)acrylate may be in the range from 50 to 300, for example 120 to 280 mM and the CoA concentration a fraction thereof, preferably as derivable from the preferred molar excess ratios in favour of (meth)acrylate just mentioned.

Other components required are also present (e.g. a $Mg^{2+}$ salt, such as $MgCl_2$; ATP (preferably in hypostoichiometric molar amounts in relation to the (e.g. alkaline metal, such as sodium) (meth)acrylate, e.g. in less than one $5^{th}$ of the molar amount of the (meth)acrylate, e.g. in $\frac{1}{10}$ of this amount), and of course the biocatalyst, preferably the enzyme S-acetyl CoA synthetase, which is present in an appropriate activity, e.g. 0.5 to 15 units per ml in the presence of ATP, acetate and coenzyme A at 37° C. Preferably also buffer substances are present, for example Tris buffer (tris(hydroxymethyl)aminomethane or other buffer substances that allow for the establishment of an appropriate pH, e.g. in the range from 5 to 9, such as 6 to 8 (for example, about pH 6.4 to 7.3). These include any suitable biologically compatible buffers, such as phosphate buffers and the like. However, in an alternative embodiment a buffer is not required for the reaction to occur and the absence of a buffer may be preferred to avoid contamination of the reaction mixture with buffer components.

The yield of the desired (meth)acrylyl CoA product over the bis-adduct is still improved if the coenzyme A is not added all at once but rather is added in smaller batches (the very preferred fed-batch approach) or continuously during the reaction, thus allowing for the thioester formation to take place before the addition of further Coenzyme A to the double bond of its product (meth)acrylyl CoA is possible. For example, the CoA may be added in amounts of $\frac{1}{20}$ to $\frac{1}{3}$ of the total final amount/concentration batchwise at intervals within a time period of, for example, up to 0.5 hour, e.g. $\frac{1}{10}$ of the total CoA to be used at time 0, 5 min, 10, 15 and 20 min, respectively. In addition, ATP may also be replenished at the same time as the CoA is added Where required, the enzyme may also be replenished after appropriate time periods.

Thus the hypostoichiometric concentration of free CoA is kept preferably lower than a ratio of 1:100, e.g. 1:150 of the original (meth)acrylate concentration at each single time point, e.g. at 2 mM or lower, for example approximately 1 mM or lower, and more preferably the concentration of ATP is also kept below $\frac{1}{20}$ of the initial concentration of (meth)acrylate at each time point, e.g. below 10 mM, for example at or below approximately 5 mM.

An interesting variant of the invention relates to the use of acrylic acid as only carbon source (e.g. assimilated into lactate and then pyruvate that can be used via the Krebs cycle) which in parallel is also fed into the reaction provided in Scheme III. This approach may provide especially good conditions for synthesis of (meth)acrylic esters produced according to the method or process of the invention.

Instead of providing (meth)acrylic acid or salts thereof as precursors for the reaction with the chosen alcohol optionally or preferably in the presence of a catalyst, which can be an inorganic, organic or organometallic catalyst; or preferably a biocatalyst capable of effecting the transfer of an alcohol moiety from an alcohol starting material as defined above or below to (meth)acrylyl CoA under removal of the CoA moiety, it is also possible to use appropriate starting materials derived from biomass. These precursors are the product of biological processes (including but not limited to waste biomass materials such as agricultural materials capable of being treated, for example hydrolysed, to release appropriate starting materials) and can first be converted via biochemical pathways into (meth)acrylyl CoA. Examples are sugars (e.g. from waste biomass materials, starch, cellulose or other polysaccharides), polyols (e.g. from fats), organic acids (e.g. from metabolism or from fatty acid ester hydrolysis), amino acids or the like. The (meth)acrylyl CoA can then be converted to (meth)acrylic esters as described herein. As biomass is renewable, this approach is basically very advantageous regarding sustainable development and environmental protection. In principle and advantageously it is also possible to derive other starting materials, especially the alcohols that are free of positively chargeable or charged groups, especially as defined above or below, from biochemical pathways with biomass starting materials. For practical reasons, however, these starting materials may be added as such.

Some examples of possible metabolic reaction pathways and possible junction points as well as enzymatic activities where precursors can be fed in for the synthesis of esters according to the invention are shown in Scheme I above as well as in Scheme IV presented below:

SCHEME IV:

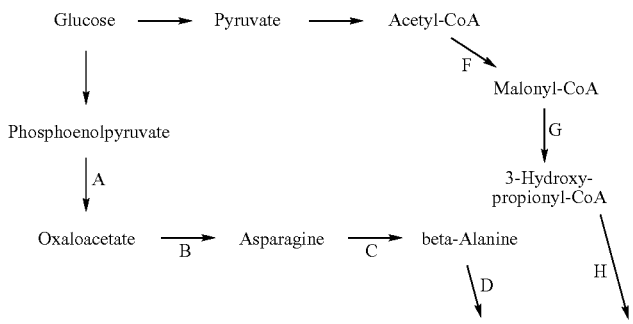

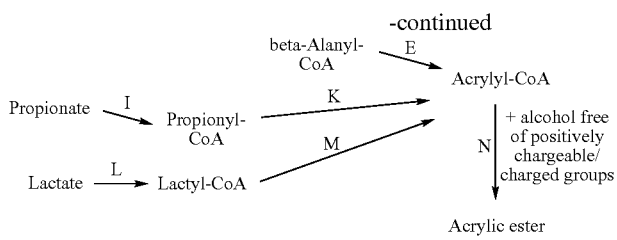

Here, the capital letters A to N preferably indicate the following enzyme activities:
A: phosphoenolpyruvate carboxykinase;
B: aspartate aminotransferase;
C: aspartate decarboxylase;
D: CoA transferase;
E: beta-alanyl CoA-ammonia lyase;
F: acetyl CoA-carboxylase;
G: malonyl CoA-reductase;
H: 3-hydroxypropionyl CoA-dehydratase (= acrylyl CoA-hydratase);
I: (acetyl) CoA-synthetase or (acetyl) CoA-transferase (which may be part of an enzyme complex such as OS17 in WO 02/042418);
K: propionyl CoA-reductase (which may be part of an enzyme complex such as OS17 in WO 02/042418);
L: CoA synthetase or CoA transferase;
M: lactyl CoA-dehydratase;
N: biocatalyst that is capable of effecting the transfer of an alcohol moiety from an alcohol starting material as defined above or below to (meth)acrylyl CoA under removal of the CoA moiety.

For the synthesis of methacrylic esters, it is, for example, possible to use isobutyric acid or metabolic precursors thereof instead of propionic acid in Scheme IV as point of junction or as starting material.

Other methods are possible, e.g. using the route of oxidation of propylene which can be possible using *Mycobacterium convolutum* or genetic material for biocatalysts and biocatalysts obtainable therefrom to acrylate, the oxidation of allyl alcohol to acrylate (e.g. using *Pseudomonas fluorescens* or *Nocardia coralline* or genetic material for biocatalysts and biocatalysts obtainable therefrom) or acrylonitrile or methacrylonitrile using bacterial nitrilase or nitrile hydratase in combination with amidase activities, by for instance *Rhodococcus ruber* or *Rhodococcus rhodochrous*, respectively.

The corresponding pathways and enzymic activities may be the result of gene expression (including transcription and translation and possible posttranslational modification) of nucleic acids that form part of the natural nucleic acid and genetic equipment of organisms, especially plants (or plant tissues) or more preferably microorganisms (especially unicellular organisms), most especially prokaryotes, e.g. bacteria, or (at least during a part of their life cycle) unicellular eukaryotes, for example fungi, such as yeasts, or they may be the result of the transformation of such cells (which are then becoming "host cells" for the introduced exogenous nucleic acids, that is genetically modified organisms (GMO)) comprising "exogenous" nucleic acids from other organisms (e.g. animals, such as rodents, or humans) or analogues thereof with the required sections coding for and capable of expressing the corresponding biocatalyst activities, preferably with recombinant nucleic acids, e.g. with vectors (e.g. plasmids, cosmids, viral or virus derived vectors or the like) that, in addition to one or more sections coding for the biocatalyst activities required for the synthesis of (meth)acrylic esters according to the process of the invention, or precursors thereof, may comprise one or more of repressor, activator, promoter and/or transporter sequences or other sequences required or useful for the integration, maintenance, transport within the cell or through cellular membranes, posttranslational modification and especially expression of the encoded polypeptides and their activities as well as optionally genetic markers allowing for selection (such as galactosidase or antibiotic resistance coding sequences) especially recombinant nucleic acid constructs carrying one or more of the genetic information constituents required for the biosynthesis of the corresponding enzymatic activities.

Examples of possible polypeptides and the underlying genetic information/nucleic acids that can be used to obtain enzyme activities directly useful in their parent organisms or useful in the transformation of different host cells are given in or can be deduced from WO 02/042418, and this disclosure and especially the corresponding nucleic acid and amino acid sequences as well as the methods therein for obtaining them or analogues thereof are incorporated by reference herewith. Methods useful in gene technology, especially for isolation, recombination, expression, transformation etc., are known to the person skilled in the art and can, for example, be based on or make use of the knowledge, methods and reagents disclosed in Sambrook et al., Molecular Cloning—A Laboratory Manual, 2nd edition, Cold Spring Harbor Press, 1989, or in in Gassen et al., "Gentechnische Methoden—Eine Sammlung von Arbeitsanleitungen für das molekularbiologische Labor" (translation: "Genetic Engineering Methods—a Collection of Working Protocols for the Molecular Biology Laboratory"), Spektrum Akademischer Verlag, Heidelberg 1999, in F. M. Asubel (Hg.) "Short Protocols in Molecular Biology", 3rd ed., New York, Wiley 1997; or in Asubel et al., "Current Protocols in Molecular Biology", Vol. 1-3, Greene Publishing Associates and Wiley-Interscience, New York, 1987.

As an example, a hitherto unknown isolated enzyme with a biocatalytic activity useful in the present invention (e.g. a lipase, esterase (such as acetyl choline esterase), transferase (such as choline acetyl transferase) or synthetase, especially Coenzyme A synthetase (such as S-acetyl CoA synthetase), protease or acylase (such as aminoacylase), may be partially sequenced, for example, using selective endoproteases for selective digestion, e.g. endoprotease Lys-C, endoprotease Glu-C, chymotrypsin, thermolysin or preferably trypsin (cleaving C-terminally from the basic amino acids arginine or lysine) and, after separation, e.g. electrophoretically on a gel or by chromatography (e.g. HPLC), determining the terminal sequences of the resulting peptides, e.g. by exopeptidases, e.g. carboxypeptidases, such as carboxypeptidase A, B or P). Preferred is tryptic digestion, then MS/MS analysis (TOF). The sequences thus obtained can then be used e.g. for finding corresponding coding nucleic acid (e.g. RNA or especially DNA) sequences or their non-coding counter strands, which may then be used to design primers to (e.g. by hybridization with genomic or partially (e.g. restriction endonuclease) digested DNA) find longer pieces of DNA coding for the corresponding enzyme (or the corresponding non-coding sequences from the partner strand in double-stranded DNA) which may then be pieced together (e.g. by gene walking) to a complete coding nucleic acid; or from cDNA libraries. By a combination of methods such as those depicted in the references mentioned in the last paragraph it is then possible to isolate the DNA coding for a polypeptide having one of the desired activities.

Alternatively, synthetic or isolated DNA (e.g. cDNA) of already published sequences coding for the corresponding biocatalytic activities, e.g. enzymes, for example lipase, esterase (such as acetyl choline esterase), transferase such as choline acetyltransferase or synthetase, especially CoenzymeA synthetase such as S-acetyl CoA synthetase activity, protease or acylase (such as aminoacylase), and/or transporters, e.g. for larger esters with functional groups such as amide, hydroxy, ether, ketone or ester groups, may be used and integrated into vectors.

The term "nucleic acid" refers to polynucleotides, especially DNA. Where recombinant nucleic acids are mentioned, this is intended to mean specifically nucleic acids in the form of appropriate vectors, as well as the products resulting therefrom in the transformed host cells (e.g. due to integration into the genome including also plasmids or the like and concomitant changes, recombination or comparable events). Recombinant nucleic acids useful in the transformation of host organisms are, for example, vectors (e.g. plasmids, cosmids, viral or virus derived vectors or the like) comprising the coding sequences necessary for expression of the corresponding biocatalyst activities.

In general, "recombinant", wherever used in the context with a nucleic acid or especially DNA, is preferably having its customary meaning, for example including (1) a sequence that is not naturally occurring in the organism in which it is introduced or especially expressed or (2) a sequence made by an artificial combination of two otherwise separated shorter sequences (e.g. by insertion of a coding sequence into a plasmid or other vector). The artificial combination may be achieved by chemical synthesis and/or preferably by the artificial manipulation of isolated segments of nucleic acids, e.g. by genetic engineering techniques such as partial digestion, e.g. with endonucleases, ligation, splicing, or the like. "Recombinant" is also used to describe nucleic acid molecules that have been artificially manipulated but contain the same regulatory sequences and coding regions that are found in the organism from which the nucleic acid was isolated.

The invention relates also especially to an (at least partially) biosynthetic route to any one or more of the (meth)acrylate esters which are free of positively chargeable or charged groups using one or more genetically modified organism(s) (GMO) as well as the corresponding GMO, preferably selected from genetically modified preferably (at least during parts of its life cycle) unicellular microorganisms (especially a prokaryote, most preferably a bacterium, or a fungus, most preferably a yeast, but also insect cells may be employed, e.g. using baculovirus-expressed systems), which (either already in its natural form or after transformation with one or more appropriate nucleic acids) comprise a) a nucleic acid (especially a DNA) from a prokaryote, preferably a bacterium; or less preferably a eukaryote, such as yeast, other insect, fungal or plant cells, fungal or plant tissues or plants; each of which will enable the GMO to biocatalytically convert a biomass starting material (preferably as defined above, e.g. a polyol or a sugar such as glucose) preferably to lactate and further to (meth)acrylyl CoA;

b) in combination with one or more (preferably recombinant) nucleic acids (especially a DNA) coding for an enzyme capable of effecting the transfer of an alcohol moietyl from an alcohol starting material as defined above or below to (meth)acrylyl CoA under removal of the CoA moiety, such as a transferase (EC 2) or hydrolase (EC 3), e.g. lipase, esterase, protease or acylase (such as aminoacylase) (including coding for one or more such enzymes). These enzymes can be derived from a prokaryote such as a bacterium, a eukaryote or a higher organism, such as lipase from *Candida* spp., esterase or choline acetyl transferase from mammalian cells, and they can be supplied to the reaction as such. Alternatively, it can also be produced biosynthetically from appropriate starting materials derived from biomass.

Advantageously, the GMO, if not already displaying such activity, is also modified in addition to enable the chosen alcohol(s) used as starting material, as defined hereinabove or below, to enter the cell and/or where required to allow the obtainable (especially resulting) ester product(s) to leave the cell. The embodiments of this concept of combining the activities or recombinant genetic materials from microorganisms, especially prokaryotes or unicellular eukaryotes or plants with those of higher organisms, e.g. taking genetic material coding for an enzyme capable of effecting the transfer of an alcohol moiety from an alcohol starting material as defined above or below to (meth)acrylyl CoA under removal of the CoA moiety for the preferred synthesis of the (meth) acrylic esters such as the resulting GMO and their use in the manufacture of (meth)acrylic esters (as defined above or below) and/or processes or methods using these GMOs in the manufacture of (meth)acrylic esters (as defined above or below), are especially preferred variants of the invention, as especially the use of such GMO comprising recombinant nucleic acids coding for required activities in addition to the other required activities already present or also recombinantly integrated into said GMO in processes for the manufacture of (meth)acrylic esters as defined above or below. The invention also relates to the manufacture of the respective GMO, especially unicellular organisms, especially prokaryotes, such as bacteria, e.g. *E. coli*, or fungi or single cell eukaryotes, e.g. yeasts, comprising combining one or more nucleic acids encoding the activities mentioned in this paragraph under a) and b). Preferred is a transformed prokaryote, especially a bacterium, or a transformed fungus, preferably a yeast, comprising one or more (natural or recombinant) nucleic acids coding for enzymes capable of effecting the transfer of an alcohol moiety from an alcohol starting material as defined above or below to (meth)acrylyl CoA under removal of the CoA moiety.

The product (meth)acrylic esters (as defined above or below) when produced in cells (e.g. GMO as mentioned in the last paragraphs) may be isolated from the supernatant directly (also in the case of permeabilized cells) or (if it is not readily leaving the cells) after permeabilization of the cells (which may also allow for the entry of starting materials), e.g. with appropriate surfactants or pore proteins (e.g. from the mammalian complement system) or after (e.g. chemical or mechanical) disruption of the cell membrane, e.g. using one or more methods employing a homogenizer, a blender, ultra sonic disruption or the like. In the case of disrupture, remaining cells might be used for further production, e.g. if only parts of the culture are used for disruption, continuous reaction is possible but batch-wise or fed-batch wise production is preferred, while in the other cases the process may be led either in a continuous or a batch-wise way, the product being isolated from the supernatant.

Isolation of the product or product acrylic esters in any case, also in the case of in vitro synthesis, may take place using standard methods, e.g. using chromatography (especially including a step of ion exchange chromatography), electrodialysis, solvent washing, extraction, partitioning or the like, or combinations of such methods. Alternatively, it may be possible to polymerise the corresponding (meth) acrylic ester monomers in situ, either to yield a homopolymer or with the addition of other polymerisable monomers, for example acrylamide, styrene or the like, without need for prior purification. In a particularly preferred method of product recovery that is especially applicable to the production of volatile (meth)acrylic esters, the vapour over the reaction mixture is condensed, and if necessary or desired unreacted starting material re-cycled to the reactor after separation in part or in full from the product stream. This process can be aided by the application of heat or vacuum or both. As an example, the vapour from an aqueous mixture of ethanol and ethyl acrylate forms an azeotrope that is composed of 10.1% water, 48.3% ethanol and 41.6% ethyl acrylate by weight (Azeotropic Data III, compiled by L H Horsley, Advances in Chemistry Series 116, American Chemical Society, Washington D.C., 1973). Adjusting the pressure to 165 mmHg this ratio changes to 8.6% water, 36.3% ethanol and 55.1% of the desired ethyl acrylate ester. Further concentration of the ester relative to the other components is a known technique to those skilled in the art, and would allow re-cycle of separated ethanol to the reactor. By removal of the acrylic ester in this fashion, higher conversion efficiencies can be expected to result by moving the equilibrium in favour of the forward reaction. For water/n-butanol/n-butyl acrylate mixtures, the weight ratios for azeotropic vapours are 50%137.6%112.4% at atmospheric pressure, changing to 41%126%133% at 100 mmHg.

It is also possible to reduce or (where the corresponding biocatalytic activities are not required for the survival of living cells where such are used) remove the activity of certain biocatalysts, e.g. by using one or more methods such as gene disruption, antisense nucleic acids, mutation, knock-out methods or administration of appropriate reversible or irreversible inhibitors, or the like in order to allow for the accumulation of desired products or intermediates, e.g. acrylyl CoA or methacrylyl CoA, by blocking metabolic pathways that lead away from these products other than the way used for their synthesis and preferably the further reaction to the (meth)acrylic acid esters as defined above or below (e.g. one or more of the reactions catalyzed by or leading through the enzyme activities E, H, K or M shown in Scheme IV). This may be useful to achieve a higher availability (concentration) of precursors required for the synthesis of the (meth)acrylic esters as defined above or below, e.g. (meth)acrylyl CoA.

While the borders for a distinction of in vitro and in vivo reactions may appear blurred in specific cases, these expressions are preferably defined as follows:

"In vitro", where used in this disclosure, preferably means that the corresponding process is carried out with cells or cell components (up to purified enzymes) that are no longer viable (that is, no longer display all (meaning none or less than all) signs of life, that is motility, propagation, metabolism, heredity with or without mutability, and excitability) or with cell free systems, e.g. enzyme solutions. In vitro can also mean without components (e.g. enzymes, organelles or the like) of living organisms, e.g. purely in the presence of the starting materials (such as alcohols and (meth)acrylyl CoA).

"In vivo" means that a process takes place in the presence or preferably mainly inside of living, substantially intact organisms or cells (which show the features of life as defined in the last paragraph). The term "substantially intact" is also intended to include organisms or cells with permeabilized membranes e.g. by means of surfactants or pore proteins or the like, as far as still the features of life defined in the last paragraph are still present.

Where (at least substantially) intact, such as (especially transformed, resulting in GMO) cells or organisms are to be used, it may in certain cases (e.g. where the starting material alcohols as defined above or below are not readily membrane permeating or where this leads to improved transport) be useful if these have a one or more appropriate transporter molecules (especially one integrated into their respective cell membranes, e.g. as membrane protein) that allows for easy passage of the alcohols through cellular membranes.

Where required or useful (e.g. to accelerate the transport, or to remove the product from an intracellular equilibrium), also one or more transporter molecules for the (meth)acrylic ester products are present, either already as part of the natural equipment of the used organisms or as the result of genetic recombination and transformation.

Alternatively, cells may be used that have permeabilized cell membranes (e.g. by means of surfactants or pore proteins as already mentioned).

If substantially intact organisms or cells are used as biocatalysts, e.g. in the process of a fermentation, a lower (usually meaning only minimal or no) addition of co-factors is required, so that this is a particularly preferred embodiment of the invention (while sometimes it may be necessary to contribute nutrients including precursors or vitamins useful in the biosynthesis of said co-factors). One of the reasons is that the cells are capable of recycling and sometimes even synthesizing the required co-factors (e.g. ATP, $NAD(P)^+$, $NAD(P)H$, FAD, FADH, Coenzyme A) by themselves.

However, the organisms/cells usually react very sensitively to high concentrations of organic substrates (substrate or product inhibition, solvent deactivation). Therefore, where specific solvents have to be used or where substrates or products might lead to a reduced reaction rate or yield, also the use of partially purified systems may be advantageous which forms a different embodiment of the invention. For partial purification, the cells are disrupted, and where desired the cell debris is removed and a cell-free extract is obtained.

The fermentation time is preferably so selected that an optimum with respect to the desired biocatalyst (e.g. capable of effecting the transfer of an alcohol moiety from an alcohol starting material as defined above or below to (meth)acrylyl CoA under removal of the CoA moiety and/or (meth)acrylyl CoA synthesis) activity is achieved. For example, when the cell density has reached an adequate value, the cultivation is discontinued. The culture broth is separated off in known manner, e.g. by centrifugation, and the sedimented cells are broken down in customary manner, e.g. by shaking with fine particular material such as glass beads, by ultrasound treatment, using a homogenizer, a blender or a French press, or the like. Insoluble cell components and, if used, particular material such as glass beads or the like, are optionally removed, e.g., by centrifugation or filtration, and the particle and cell debris free residue is used as the biocatalyst activity source (crude extract). The residue, as a biocatalyst activity-comprising crude extract, can be used directly in the process according to the invention. Advantageously, however, in order to remove nucleic acids (viscous solutions) and other impurities or interfering components (e.g. inhibitors or disturbing enzyme activities or the like) the crude extract is subjected to further purification in order to obtain the biocatalytic activity or activities useful in the invention in more purified (more enriched) form. Preferably, the crude cell extract is subjected to one or more purification steps that, as such, are known in the art in order to remove interfering components from the extract. Alternatively the biocatalyst capable of effecting the transfer of an alcohol moiety from an alcohol starting material as defined above or below to (meth) acrylyl CoA under removal of the CoA moiety may be secreted by the microorganism into the culture medium, whereby it can quite readily be recovered and used as a crude preparation thus. Crude preparation is any solution comprising the biocatalyst capable of effecting the transfer of an alcohol moiety from an alcohol starting material as defined above or below to (meth)acrylyl CoA under removal of the CoA moiety that includes contaminating components such as growth medium components or compounds present as a result of metabolism by the microorganism.

The term "purified" means preferably "in at least partially purified form" (="in enriched form") or, more preferably, purified in the stricter sense, that is, in practically isolated form (e.g. in the case of isolated proteins, such as enzymes capable of effecting the transfer of an alcohol radical from an alcohol starting material as defined above or below to (meth) acrylyl CoA under removal of the CoA moiety or CoA synthetase) especially with more than 50, most especially more than 95% purity by weight compared to other oligo- or polypeptides present).

Further, the invention relates to the use of the mentioned organisms, which (here as in all other places where organisms are mentioned in the present disclosure) may preferably be GMO as mentioned above, such as (preferably transformed) plants or plant parts or plant tissues or insect cells or especially microorganisms, especially cells, more especially host cells for the respective recombinant genetic material (such as bacteria, e.g. *E. coli, K. lactis, Lactobacillus* spp., *Propionibacterium shermanii, Clostridium propionicum, Zymomonas mobilis, Bacillus* spp. or *Bacillus coagulans, Rhodococcus* spp., *Pseudomonas* spp., *Streptomyces* spp., *Megasphera* spp., for the case of extreme (e.g. temperature and/or pH) conditions archebacteriae, yeasts or other fungi, such as *Saccharomyces cerevisiae, Kluyveromyces* spp., *Pichia* spp., *Hansenulo* spp., *Candida* spp., *Trichosporon* spp. or *Yamadazyma* spp.) transformed with appropriate nucleic acids, in the production of one or more of the required biocatalysts, especially a biocatalyst capable of effecting the transfer of an alcohol moiety from an alcohol starting material as defined above or below to (meth)acrylyl CoA under removal of the CoA moiety or alternatively or in addition with synthetase, especially Coenzyme A (especially S-acetyl coenzyme A) synthetase activity, which may then be used in the manufacturing methods (in vitro, in vivo or combined) according to the invention for the synthesis of (meth)acrylic esters as defined above or below.

Unless indicated otherwise already above or further below, further general terms, symbols and names used in the description of the present invention preferably have the following meanings (where more specific definitions, in each case separately, or in combination, may be used to replace more general terms in order to define more preferred embodiments of the invention, also as regards general terms, symbols and names and their explanations or preferred meanings already given above):

A catalyst useful in the method or process according to the invention may be any component capable of effecting the transfer of the alcohol moiety of an alcohol starting material as defined above or below to (meth)acrylyl CoA under removal of the CoA moiety.

The term "biocatalyst", e.g. in "biocatalyst capable of effecting the transfer of an alcohol moiety (meaning a moiety including the oxygen of the OH group reacting) from an alcohol starting material as defined above or below to (meth) acrylyl CoA under removal of the CoA moiety" or "biocatalyst with (=having) transferase activity", where used herein, relates to a biocatalyst having the respective (e.g. an enzyme capable of effecting the transfer of an alcohol moiety from an alcohol starting material as defined above or below to (meth) acrylyl CoA under removal of the CoA moiety, such as a transferase, lipase, esterase, acylase or protease) activity, especially an enzyme, most preferably a polypeptide, with said transferase activity, preferably as described herein. If not stated otherwise, all these terms include not only the naturally occurring, "authentic" sequence of a polypeptide of the invention, which are the preferred embodiments of the invention, but also all mutants, variants and fragments thereof which exhibit the respective activity, preferably with at least 1%, more preferably at least 10% of the relative activity of the natural (parent) enzyme (especially in isolated form) from which they are derived. The terms lipase, protease, acylase, transferase and esterase are preferably as defined above in the paragraph on hitherto unknown isolated enzymes.

The term "biocatalyst with [="having", "that has"] synthetase activity" preferably relates to biocatalyst capable of transferring an carboxylic acid moiety, especially acrylate and/or methacrylate, to the sulfhydryl group of Coenzyme A under consumption of energy derived from nucleoside trisphosphates, such as ATP, e.g. Coenzyme A synthetase, such as S-acetyl Coenzyme A synthetase.

"A biocatalyst capable of effecting the transfer of an alcohol moiety from an alcohol starting material as defined above or below to (meth)acrylyl CoA under removal of the CoA moiety" especially means that the corresponding biocatalyst, preferably an enzyme, is active in standard assay systems used for determining the activity of the desired enzyme which catalyses the reaction native to that particular enzyme Preferred as such a biocatalyst is an EC group 2 enzyme, that is a "transferase", including, but not restricted to, transaminases, transamidases, transketolases, transphosphorylases or choline acetyl transferase that are known to catalyse the movement of a chemical group from one compound to another, or an EC class 3; "hydrolase" which are also capable of catalysing transesterification reactions. Suitable hydrolase enzymes are, for example, lipases from *Candida antartica* (CAL B), porcine pancreatic lipase (PPL), *Candid rugosa* (CRL) *Pseudomonas cepacia* (PCL) and the like; esterases such as pig liver esterase (PLE) acetyl choline esterase; also proteases such as subtilisin, protease, for instance from *Aspergillus* spp., *Bacillus* spp., *Rhizopus* spp and other hydrolases such as penicillin amidase or (especially L-amino) acylase may be suitable enzymes to catalyse the transfer. Biocatalysts useful in the invention here or in at least one of the subsequent assays advantageously show an activity of more than 0.01 nmoles/min per mg protein, more preferably of 0.1 nmoles/min per mg of protein, still more preferably of 0.4 nmoles/min per mg. or protein. For instance when testing for choline acetyl transferase activity, for the determination of the activity of the enzyme (that are also applicable in the case of membrane bound or associated enzyme, e.g. measuring homogenates) methods are known, e.g. using $^{14}$C-labelled acetyl CoA, see for example Fonnum, F., Biochem. J. 115, 465-79 (1969) or Fonnum, F., J. Neurochem. 24, 407 (1975), or Rylett et al., J. Neurochem. 45, 611-20 (1993), for example determining the initial reaction velocities at 37° C. in a 40 µl reaction mixture containing 5-1200 µM [1-$^{14}$C]acetyl CoA (Amersham), 0.1-3.5 mM choline, 0.2-10 ng biocatalyst with choline acetyltransferase activity, 50 mM sodium phosphate (pH 7.4), 250 mM NaCl, 1 mM EDTA and 0.5 mg/ml BSA (see Ohno et al., Proc. Natl. Acad. Sci. USA 98(4), 2017-22 (2001)). In one preferred exemplary method, in order to test the usefulness of a biocatalyst for synthetic purposes, for example first the choline acetyl transferase activity of the biocatalyst to be tested is determined using its natural substrate acetate. Then a solution of 7 mM choline chloride is prepared in pH 7.46 buffer (1.1 mM $Na_2HPO_4$/0.7 mM $NaH_2PO_4$). The choline solution (3 ml) is incubated at 37° C. for 15 min. Acetyl CoA (2 mg, 2.5 μmoles) and 0.1 ml of pH 7.4 choline acetyltransferase or the biocatalyst to be examined (for example with an activity of e.g. approximately 5.5 to 20 nmoles/min regarding acetate) is added and the absorbance measured with time. On completion of the reaction, the reaction mixture is stored frozen until analysed by ion chromatography (IC). IC analysis is carried out on a Dionex DX-300 instrument with an IonPac CS12A column, a mobile phase of 90% 20 mM methanesulphonic acid/10% of a 90% (v/v) solution of acetonitrile in water and conductivity detection (CSRS autosuppression external water mode cation regeneration system). After 435 min, 0.10 mM acetylcholine can be found with the enzyme having a presumed initial activity of 20 nmoles/min. A biocatalyst having sufficient activity should, in this test system, advantageously provide more than 0.02 mM acetylcholine under these conditions. More preferably, the activity with methacrylyl-CoA or preferably acrylyl-CoA should be more than 10%, still more preferably more than 50% in any used test system of the activity with acetyl-CoA for a biocatalyst with choline acetyltransferase activity that is particularly useful in a process or method of the present invention. Examples for enzymes with choline acetyltransferase activity are those from *homo sapiens*, or other vertebrates, such as mice or especially rat, or more generally from other metazoa. Also recombinant Choline acetyl transferases are included here, such as advantageously recombinant rat choline acetyl transferase AG220 from Chemicon International Inc., Temecula, Calif., or analogues thereof.

For testing lipase activity, also known protocols may be used, e.g. as described in Biotechnology Techniques 10(4), 283-286, using e.g. 1-undecanol, 9-decen-1-ol, 10-undecen-1-ol. 13-tetradecen-1-ol, oleyl alcohol or stearyl alcohol and on the other hand, methylacrylate or methylmethacrylate as substrates.

Alternatively, esterase or lipase activity can, for example, be determined by measuring the amount of fatty acid released by the test enzyme over a given period from a triolein emulsion (olive oil) at 37° C. at pH 7.0 and in the presence of 0.025% (final concentration) sodium taurocholate. To ensure that all the fatty acids released are measured, the final titration is carried through to pH 9.0, and a blank titration on the substrate emulsion carried out to determine any acids not resulting from lipase activity. One unit is defined as the amount of enzyme releasing one micromole of fatty acid per minute under the conditions of the assay. The specific activity is expressed in international FIP units per mg of enzyme. As equipment, an automatic titrator, a high speed homogenizer, a water bath and a magnetic stirrer are used. Reagents are gum arabic acacia Eur. Ph. Grade, triolein (olive oil) USP, sodium taurocholate FIP grade. 110 g of gum arabic or acacia and 125 g calcium chloride are dissolved in distilled water and made up to 1 l, followed by stirring for 30 min at room temperature to solubilise the material and centrifugation or filtration to produce a clear solution. Store at 5° C. in a refrigerator. To obtain the substrate solution, to 130 ml of triolein 400 ml of the gum arabic or acacia solution is added, followed by emulsification at high speed in a blender at temperatures below 30° C. Using microscopic control, 90% of the droplets should be of less than 2 to 3 micrometer in diameter, the remainder not exceeding 10 micrometer. For the enzyme solution, the enzyme to be tested is dissolved in 1% saline, preferably in a concentration corresponding to 2.4 to 3.6 U lipase per ml. For the test, 24 ml of substrate, 2 ml taurocholate solution (0.5 g taurocholate dissolved in 100 ml distilled water) and 9 ml distilled water are placed in a reaction vessel and equilibrated to 37° C. with magnetic stirring. The pH electrode and the tip of the burette are immersed in the solution and the pH is adjusted to 6.7 with NaOH (0.02 M). The automatic burette is zeroed and 5 ml of enzyme solution are added, the timer is started and the pH maintained at 7.0 as the reaction proceeds. After 10 min the pH is abruptly brought to 9.0 by manual addition of NaOH (0.02 M). This is done quickly (approx. 30 seconds) and the total volume of NaOH recorded ($N_1$). A control titration is made using water in place of enzyme and the titration determined ($N_2$). Manual titration may be used where pH 7.0 is maintained throughout by manual addition of NaOH. For calculation of the activity, 1 ml of NaOH corresponds to the neutralisation of 20 micromol of fatty acids. For example, where 5 ml enzyme solution liberates $N_1$ ml and the control $N_2$ ml of NaOH and wherein $N_1$ is the sample, $N_2$ is the control and C is the enzyme concentration in mg/ml, then the specific activity is determined according to the following formula:

$$\frac{(N_1 - N_2) \times 20}{10 \times 5 \times C} = FIP\ U/mg.$$

(Alphamerix Ltd., Cambridge, UK).

"A biocatalyst with synthetase activity" especially means that the corresponding biocatalyst, preferably an enzyme, is active in standard assay systems used for determining the activity of acetyl CoA synthetase. For example, the following coupled enzyme test monitoring the formation of AMP may be used to determine acetyl CoA synthetase activity: The assay consists of ATP (2.5 mg, $5\times10^{-3}$ mmol), CoA (0.46 mg, $6\times10^{-4}$ mmol), $MgCl_2$ (4 mg, $2\times10^{-2}$ mmol), phosphoenolpyruvate (0.19 mg, $9.4\times10^{-4}$ mmol), KCl ($1.2\times10^{-4}$ mmol), NADP (0.25 mg, $3.6\times10^{-4}$ mmol), acetic acid ($10^{-1}$ to $10^{-4}$ mmol), acetyl coenzyme A synthetase or the biocatalyst to be tested (preferably in an activity of approximately 0.5 units), pyruvate kinase/lactate dehydrogenase (1 unit), myokinase (1 unit) and made up to a total volume of 1 ml with Tris buffer (0.25 M, pH 7.2). The reaction is monitored by observing the decrease in absorbance at 340 nm due to the oxidation of NADH to NAD+. The $V_{max}$ and binding constants are calculated by Lineweaver-Burk and Eadie-Hofstee plots. Other determination methods are possible, e.g. using acetyl-CoA formation coupled to reduction of NAD+ via malate dehydrogenase and citrate synthetase, e.g. as described by Cai et al., J. Bacteriol. 182, 2113-8 (2000) or Charles et al., Genetics 146, 9877-82 (1997). Particularly preferred is the method employed by Sigma for the testing of choline acetyl transferase activity which is a modification of the method described by Berg, P., J. Biol. Chem. 222, 991-1013 (1956): Here, acetyl CoA formed is converted with hydroxylamine into acetyl-NHOH, The latter is then mixed with a $FeCl_3$ solution to give a brown-colored product the absorbency of which is then measured at 546 nm, 1 cm light path. In brief, the final assay concentrations of the reaction mix (1.10 ml per vial) are: 136 mM potassium phosphate, 4 mM magnesium chloride, 9.1 mM ATP, 45 mM potassium fluoride, 9.1 mM potassium acetate, 9.1 mM reduced glutathione, 0.35 mM coenzyme A, 182 mM hydroxylamine and 0.02-0.04 units S-acetyl coenzyme A synthetase, the latter added in a volume of 0.1 ml after equilibration of the remaining solution at 37° C. The pH is 7.5. After addition of the enzyme, the mixture is immediately mixed and incubated for 20 min. After that, 2 ml of a 370 mM $FeCl_3$/3.3% trichloroacetic acid solution is added, followed by mixing with conversion and transfer to the measuring cuvettes. In the blank sample, acetyl CoA is missing. Preferably, a biocatalyst with S-acetyl CoA synthetase activity useful in the present invention in the preceding assay systems has an activity that is in the area of more than 0.0005 units per mg protein, more preferably in the area from 0.001 to, for example, 15 units per mg. protein, a unit being defined as the amount of biocatalyst forming 1.0 μmole of S-acetyl Coenzyme A from acetate, ATP and coenzyme A per min at 37° C. and pH 7.5. In order to test the CoA synthetase activity on a preparative scale, a reaction (e.g. at a 7 ml scale) can be started and conducted in 10.8 mM sodium phosphate/1.4 mM sodium hydroxide buffer as follows: A solution of 7.4 mM sodium acetate and 0.75 mM CoA is prepared and incubated at 37° C. for 15 min. S-acetyl-coenzyme A synthetase, either from Sigma, catalogue No. A 1765 from Bakers yeast, or the biocatalyst to be tested (e.g. 0.2 mg) and 28.4 mg ATP is added. The mixture (pH about 7.36) is then incubated at 37° C. in quartz cuvettes and the absorbance of the mixture at 232 nm is measured with time. For example, an initial activity of approximately 1 to 600 nmoles formation of acetyl CoA per minute or more is found in this assay. The preferred activity of this type for the preparation of (meth)acrylyl CoA (effect as (meth)acrylyl CoA synthetase activity) can advantageously be shown as described in the Examples. Preferably, the S-acetyl CoA synthetase activity for formation of methacrylyl-CoA or preferably acrylyl-CoA in the presence of acrylate or methacrylate should be more than 10%, still more preferably more than 50% in at least one test system for the determination of the activity for formation of acetyl-CoA for an biocatalyst with acetyl CoA syntetase activity that is particularly useful for a process or method according to the present invention. Examples for enzymes with acetyl CoA synthetase activity are acetyl CoA synthetase from yeast, e.g. baker's yeast (obtainable e.g. from Sigma or Roche), from bacteria, e.g. *Salmonella enterica, Sinorhizobium meliloti, Rhodospirillum rubrum*, from higher animals, e.g. beef heart or pigeon liver, or plants.

Other enzyme activities can be tested as described herein and/or as described in Standard works, such as the "Methods in Enzymology" series, Academic Press (now belonging to Elsevier).

Where acids are mentioned, this is intended to encompass both the free acids as well as salts thereof, or mixtures thereof, e.g. metal- or ammonium salts or the like. Usually within the present disclosure acids are referred to in the form of the corresponding anions, e.g. as acrylate or acetate.

"(Meth)acrylyl" means acrylyl and/(preferably:) or methacrylyl. (Meth)acrylate means acrylate and/(preferably:) or methacrylate and/or their salts. (Meth)acrylyl means acrylyl, methacrylyl or methacrylyl and acrylyl.

For esters of acrylic acid and/or (preferably or) methacrylic acid (or of (meth)acrylic acid) (also named acrylic, methacrylic or (meth)acrylic esters herein) which are free of positively charged (especially including chargeable) groups that are produced according to the process of the present invention, "free of positively charged groups" means especially free of positively charged or chargeable primary, secondary or tertiary amino groups or of positively charged quaternary amino groups. Preferred as such esters are one or (in the same method or process of manufacture less preferably) more (meth)acrylic (acid) esters selected from unsubstituted or substituted (meth)acrylic (acid) $C_1$-$C_{20}$-alkyl alcohol esters wherein the $C_1$-$C_{20}$-alkyl is unsubstituted or substituted by one or more, especially up to three, moieties independently selected from hydroxy, $C_1$-$C_7$-alkoxy, $C_2$-$C_7$-alkanoyolxy, $C_2$-$C_7$-alkanoylamino, oxo, carbamoyl, N—$C_1$-$C_7$-alkylaminocarbonyl, N,N-di-($C_1$-$C_7$-alkyl)-aminocarbonyl and $C_1$-$C_7$-alkoxycarbonyl, is linear, branched one or more times and may comprise one or more double bonds; more preferred are n-butyl(meth)acrylate (very preferred), ethyl (meth)acrylate (preferred), methyl(meth)acrylate (preferred), or further n-propyl, isopropyl, isobutyl, sec-butyl, tert-butyl, 2-ethylbutyl, n-pentyl, isopentyl, 1-methylpentyl, 1,3-dimethylbutyl, n-hexyl, isoheptyl, 1-methylhexyl, 2-ethylhexyl, stearyl or 2-hydroxy ethyl (meth)acrylate, or (though less preferably) mixtures of two or more of these. Highly preferred are the n-butyl or the ethyl ester of especially acrylic acid, further of methacrylic acid or both.

In "alcohols that are free of positively charged groups" and that are preferably used as starting material(s) in the method or process of the invention, "free of positively charged groups" means especially free of positively charged or chargeable primary, secondary or tertiary amino groups or of positively charged quaternary amino groups. Preferred as such alcohols are one or (in the same method or process of manufacture less preferably) more $C_1$-$C_{20}$-alkyl alcohols wherein the $C_1$-$C_{20}$-alkyl is unsubstituted or substituted by one or more, especially up to three, moieties independently selected from hydroxy, $C_1$-$C_7$-alkoxy, $C_2$-$C_7$-alkanoyolxy, $C_2$-$C_7$-alkanoylamino, oxo, carbamoyl, N—$C_1$-$C_7$-alkylaminocarbonyl, N,N-di-($C_1$-$C_7$-alkyl)-aminocarbonyl and $C_1$-$C_7$-alkoxycarbonyl, is linear, branched one or more times and may comprise one or more double bonds; more preferred are n-butanol (very preferred), ethanol (preferred), methanol (preferred), or further n-propanol, isopropanol, isobutanol, sec-butanol, tert-butanol, 2-ethylbutanol, n-pentanol, isopentanol, 1-methylpentanol, 1,3-dimethylbutanol, n-hexanol, isoheptanol, 1-methylhexanol, 2-ethylhexanol, stearyl alcohol or 2-hydroxy ethanol, or (though less preferably) mixtures of two or more of these. Highly preferred are n-butanol or ethanol.

In a further preferred embodiment of the invention, the invention relates to a process or method for the manufacture of ethyl(meth)acrylate, especially acrylate, or n-butyl (meth) acrylate, especially acrylate (preferred), or methyl(meth) acrylate, especially methyl acrylate (preferred), comprising reacting ethanol and/or n-butanol (preferred) and/or methanol (preferred) and acrylyl-CoA and/or methacrylyl-CoA, preferably acrylyl-CoA, optionally or preferably in the presence of a catalyst which can be an inorganic, organic or organometallic catalyst; or most preferably a biocatalyst with transferase activity, preferably as defined above, which is taking place in vitro. Alternatively, the corresponding process or method taking place in vivo is preferred. Also, the corresponding process or method partially taking place in vitro, partially taking place in vivo is preferred (e.g. where first (meth)acrylyl CoA is formed in vivo, then (e.g. after cell disruption) the (meth)acrylyl CoA is used for the synthesis of the (meth)acrylyl esters in vitro in the presence of an enzyme capable of effecting the transfer of an alcohol radical from an alcohol starting material as defined above or below to (meth) acrylyl CoA under removal of the CoA moiety, forms a preferred embodiment of the invention.

Another preferred embodiment of the invention relates to said process or method where the biocatalyst capable of effecting the transfer of an alcohol moiety from an alcohol starting material as defined above or below to (meth)acrylyl CoA under removal of the CoA moiety is within an organism, especially a (more preferably at least during part of its life cycle unicellular) microorganism, preferably a GMO as defined above. In still one further embodiment, said organism is intact (especially at least viable as defined above), in another embodiment the organism is disrupted or permeabilized.

In yet another preferred embodiment of the invention relates to a process or method as described above wherein the (meth)acrylyl CoA is obtained by reacting coenzyme A with (meth)acrylic acid or its salts in the presence of an energy providing substance, especially ATP, and a biocatalyst with synthetase activity, preferably Coenzyme A synthetase (such as S-acetyl CoA synthetase) activity. Preferably, both reactions ((meth)acrylyl-CoA formation and subsequent transfer to an alcohol) take place in one pot, preferably during an at least partially overlapping time period, most preferably at the same time. Alternatively, the one pot reaction takes place preferably such that the reaction catalysed by the biocatalyst with synthetase (especially S-acetyl CoA synthetase) activity takes place first and the products obtainable ((meth)acrylyl CoA) are converted subsequently into ethyl(meth)acrylate, especially acrylate, methyl(meth)acrylate, especially methyl acrylate or preferably n-butyl(meth)acrylate or other acrylate (preferred) using a biocatalyst capable of effecting the transfer of an alcohol moiety from an alcohol starting material as defined above or below to (meth)acrylyl CoA under removal of the CoA moiety.

More preferred are all processes and methods mentioned above and below where the biocatalysts are enzymes, especially polypeptides, having the respective activity.

Still more preferred is any process or method described above and below wherein the (meth)acrylyl CoA is produced metabolically, especially from one or more starting materials derived from biomass (especially as described above).

Very preferred is any process or method described above or below where the production of methacrylyl CoA and/or (preferably) acrylyl CoA takes place metabolically (e.g. from free methacrylate and/or acrylate or via other metabolic precursors, such as lactyl CoA) and the conversion with a biocatalyst capable of effecting the transfer of an alcohol moiety from an alcohol starting material as defined above or below to (meth)acrylyl CoA under removal of the CoA moiety in the presence of the chosen alcohol starting material, or in each case starting materials for the biosynthesis thereof derived from biomass, to the products are conducted by means of, preferably in, a genetically modified organism (GMO) that is, as far as necessary or desired, modified to comprise the required biocatalytic activities, and where required, transporters. Preferably, this process takes place in vivo.

A further very preferred process is to carry out the biotransformations as described above in a continuous mode where the chosen alcohol is fed to a reactor containing biomass having the synthetic capability as described for a process or method according to the invention above, with continuous removal of the headspace vapours, subjecting these vapours to fractional distillation and return of the still bottoms to the reactor.

Regarding the GMO transformed with one or more nucleic acids comprising one or more sections coding for and allowing the expression of a biocatalyst capable of effecting the transfer of an alcohol moiety from an alcohol starting material as defined above or below to (meth)acrylyl CoA under removal of the CoA moiety, the invention preferably relates to such a GMO which is an insect, an insect tissue or preferably an insect tissue; a plant or a plant tissue; or preferably a (at least during parts of its life cycle unicellular) microorganism, especially a prokaryotic or a fungal microorganism, most preferably a bacterium or a yeast, wherein the nucleic acid comprising one of more sections coding for a biocatalyst with said activity is a recombinant nucleic acid.

A preferred method is using a GMO as described in any one of the paragraphs above wherein further to one or more nucleic acids comprising one or more sections coding for a biocatalyst capable of effecting the transfer of an alcohol radical from an alcohol starting material as defined above or below to (meth)acrylyl CoA under removal of the CoA moiety one or more (in one preferred embodiment also recombinant, in another endogenous) nucleic acids comprising one or more sections coding for and allowing for the expression of (S-acetyl CoA) synthetase are present.

Further embodiments of the invention are presented in the claims, preferably in the dependent claims, which are therefore included here by reference; wherein any one or more general expression, independently of the others, may be replaced with a more specific definition as provided in the present description, thus yielding yet more preferred embodiments of the invention.

The invention relates especially to the use of the enzymes mentioned in the Examples and/or the processes and reaction conditions described there for the purposes of acrylyl- or methacrylyl CoA and ethyl acrylate, methyl acrylate, and n-butyl acrylate synthesis.

EXAMPLES

The following Examples serve to illustrate the invention without limiting the scope thereof. H-CoA means the free form of coenzyme A (with the SH group), CoA the corresponding radical bound via —S— without the hydrogen.

Example 1

In Vitro Synthesis of Ethyl Acrylate a) Fed-Batch Acrylyl-CoA Preparation:

Initial Reaction Mixture for Acrylyl-CoA preparation from acrylate and H-CoA in 3.5 ml volume: The reaction is conducted in 3.3 g/100 ml TRIZMA hydrochloride (tris(hydroxymethyl)aminomethane hydrochloride, Sigma) and 0.49 g/100 ml TRIZMA base (pH 7.12 at 37° C.). The other components of the reaction mixture are as follows:

| Component | Concentration (mM) |
| --- | --- |
| $MgCl_2 \cdot 6H_2O$ | 10 |
| Sodium acrylate | 150 |
| ATP | 5 |
| H-CoA | 1 |

S-acetyl CoA synthetase (acetate thiokinase from bakers yeast, Sigma, Saint Louis, Mo., USA; catalogue No. 1765) (1.9 mg/ml) is added. Using the fed-batch approach meaning step-wise addition (feeding) of H-CoA, aliquots of H-CoA are added after 5, 10, 15 and 20 minutes, that the H-CoA and ATP concentrations in the reactor are increased by 1 mM each time. After 25 minutes a 0.154 ml sample (leaving 3.6 ml of the reaction mixture) is extracted and analysed for acrylyl CoA by HPLC (Instrumentation: Agilent Technologies HP1090L with HP1100 Variable Wavelength UV Detector and Chemstation (rev. A.06.01)

Data System; column: Luna C18 from Phenomenex, 25 cm×4.6 mm inner diameter, bead diameter 5 µm; mobile phase: A: 25 mM ammonium formate (pH 7.0), B: methanol;

gradient 5% B for 0 min, then to 30% B in 20 min; flow 1 ml/min (approximately 130 bar), oven temperature 40° C., Detector: UV at 254 nm; injection volume 5 µl, Run time 28 min; peaks are found at the following retention times: ATP approximately 3.7 min, Coenzyme A at approximately 10.5 min, acetyl CoA at approximately 14.4 min, acrylyl CoA at approximately 17.5 min, bis-adduct at approximately 15.9 min.

After 25 minutes HPLC analysis determines that 0.128% acrylyl CoA is formed after 25 minutes.

b) Preparation of Ethyl Acrylate

Batch Ethyl Acrylate Preparation:

Initial reaction mixture for ethyl acrylate preparation from ethanol and lipase using 3.6 ml of the reaction mixture prepared in Example 1 which contains 0.128% acrylyl CoA. The reaction is conducted at 37° C. The components of the reaction mixture are as follows:

| Component | Amount |
| --- | --- |
| 0.128% Acrylyl CoA solution | 3.60 ml |
| Lipase (Novozyme 435) | 0.36 g |
| 99% Ethanol | 0.24 ml |

First 0.36 g lipase (immobilised Novozyme 435; Sigma) is added to the 3.6 ml acrylyl CoA solution (0.128%). The lipase is mixed into the solution and 0.24 ml of ethanol added. The mixture is incubated at 37° C. and sampled at 1, 2, 3 and 19 hours. The samples are analysed for the formation of ethyl acrylate by headspace-GC analysis and after 3 hours the concentration of ethyl acrylate is 12 ppm.

Example 2

A solution of 0.078% acrylyl coenzyme A is prepared following the method described in example 1a. Novozym 435 (Lipase B from *Candida antarctica* produced by submerged fermentation of a genetically modified *Aspergillus oryzae* microorganism and adsorbed on a macropourous resin; Novozyme Corp., Bagsvaerd, Denmark) (100 mg/mL) and n-butanol (51 mg/mL) are added following example 1 and after 3 h at 37° C. the concentration of n-butyl acrylate is determined to be 3.2 ppm.

Example 3

A solution of acrylyl coenzyme A is prepared at a concentration of 890 ppm following a similar method to that outlined in Example 1a but prepared in water and using one third the amount of S-acetyl coenzyme A synthetase. To this, 44 mg/mL of ethanol and 100 mg/mL of Novozym 435 are added following example 1b. After 2 hours at 37° C. the concentration of ethyl acrylate is found to be 16.4 ppm.

Example 4

A solution of acrylyl coenzyme A is prepared at a concentration of 1260 ppm following the Example 3 and to this 44 mg/mL ethanol and 100 mg/mL Lipase B are added. After two hours at 37° C. the concentration of ethyl acrylate is 4.8 ppm.

Example 5

Repeating example 4 but replacing the enzyme with Lipase C2 from *Candida cylindracea* (Alphamerix Ltd) gives an ethyl acrylate concentration of 1.4 ppm.

Example 6

Replacing the Novozym 435 in example 4 with Lipase from *Pseudomonas fluorescens* (Alphamerix Ltd) results in a concentration of ethyl acrylate of 7.3 ppm.

Example 7

Acrylyl coenzyme A is prepared at a concentration of 1460 ppm following example 3. Esterification is carried out as described following example 1b but replacing the Novozym 435 with L-aminoacylase ex *Aspergillus* spp. and results in a concentration of ethyl acrylate of 22.7 ppm.

Example 8

Repeating example 7 but using protease ex *Aspergillus oryzae* results in a concentration of ethyl acrylate of 50.1 ppm Example 9

Replacing ethanol in example 7 with methanol and using Novozym 435 as the biocatalyst results in a concentration of methyl acrylate of 17.4 ppm.

Example 10

Control

Removing the Novozym 435 in example 3 results in no detectable level of ethyl acrylate being formed.

The invention claimed is:

1. A process or method for the manufacture of an ester or meth acrylate esters of acrylic acid and/or methacrylic acid which are free of positively charged groups, said process comprising reacting one or more alcohols which are free of positively charged groups with acrylyl-CoA and/or methacrylyl-CoA in the presence of a catalyst capable of effecting the transfer of an alcohol radical from an alcohol starting material as defined above (meth)acryl CoA under removal of the CoA moiety.

2. The process or method according to claim 1 wherein the catalyst is a biocatalyst capable of effecting the transfer of an alcohol radical from an alcohol starting material as defined in claim 1.

3. The process or method according to claim 1 which is conducted in vitro.

4. The process or method according to claim 1 which is conducted in vivo.

5. The process or method according to claim 1 which is conducted partially in vivo and partially in vitro.

6. The process or method according to claim 1 where the biocatalyst capable of effecting the transfer of the alcohol radical from the alcohol starting material to (meth)acrylyl CoA under removal of the CoA moiety is present in at least partially purified form.

7. The process or method according to claim 1 where the acrylyl CoA and/or (meth)acrylyl CoA is obtained by reacting coenzyme A with (meth)acrylic acid or its salts in the presence of an energy providing substance, and a biocatalyst with synthetase activity.

8. The process or method according to claim 7 where the synthetase activity is S-acetyl Coenzyme A synthetaseactivity.

9. The process or method according to claim 7 wherein the reaction catalysed by the biocatalyst capable of effecting the transfer of an alcohol radical from an alcohol starting material to (meth)acrylyl CoA under removal of the CoA moiety and the reaction catalysed by the biocatalyst with synthetase activity take place in one pot.

10. The one pot process or method according to claim 9 where the reaction catalysed by the biocatalyst with synthetase activity takes place first and the products obtainable are converted subsequently into the ester products using the biocatalyst capable of effecting the transfer of the alcohol radical from the alcohol starting material to (meth)acrylyl CoA under removal of the CoA moiety.

11. The process or method according to claim 1 where the biocatalysts are enzymes.

12. The process or method according to claim 1 wherein the (meth)acrylyl CoA precursor is produced metabolically.

13. The process or method according to claim 1 where the vapours above the reaction mixture are continuously removed and subjected to fractional distillation.

14. The process or method according to claim 1 for the manufacture of one or more (meth)acrylic (acid) esters selected from unsubstituted or substituted (meth)acrylic (acid) $C_1$-$C_{20}$-alkyl alcohol esters wherein the $C_1$-$C_{20}$-alkyl is unsubstituted or substituted by one or more moieties independently selected from hydroxy, $C_1$-$C_7$alkoxy, $C_2$-$C_7$alkanoyolxy, $C_2$-$C_7$-alkanoylamino, oxo, carbamoyl, N—$C_1$-$C_7$alkylaminocarbonyl, N,N-di-($C_1$-$C_7$alkyl)-aminocarbonyl and $C_1$-$C_7$alkoxycarbonyl, is linear, branched one or more times and may comprise one or more double bond
  where as the alcohol starting material is one or more alcohol(s) selected from the group consisting of $C_1$-$C_{20}$-alkyl alcohols wherein the $C_1$-$C_{20}$-alkyl is unsubstituted or substituted by one or more moieties independently selected from hydroxy, $C_1$-$C_7$-alkoxy, $C_2$-$C_7$-alkanoyolxy, $C_2$-$C_7$-alkanoylamino, oxo, carbamoyl, N—$C_1$-$C_7$alkylaminocarbonyl, N,N-di-($C_1$-$C_7$-alkyl)-aminocarbonyl and $C_1$-$C_7$-alkoxycarbonyl, is linear, branched one or more times and may comprise one or more double bonds.

15. The in vitro and/or in vivo use of a biocatalyst capable of effecting the transfer of the alcohol radical from the alcohol starting material to (meth)acrylyl CoA under removal of the CoA moiety to carry out the transfer of a methacrylyl and/or an acrylyl moiety from methacrylyl and/or acrylyl CoA to an alcohol as defined in claim 1.

* * * * *